United States Patent [19]

Gelman

[11] Patent Number: 4,650,716

[45] Date of Patent: Mar. 17, 1987

[54] NOVEL SALTS OF CARBOXYMETHYLCELLULOSE

[75] Inventor: Robert A. Gelman, New Castle, Del.

[73] Assignee: Hercules Incorporated, Wilmington, Del.

[21] Appl. No.: 734,013

[22] Filed: May 14, 1985

[51] Int. Cl.[4] .............................................. B32B 9/00
[52] U.S. Cl. ..................................... 428/402; 536/98; 604/368; 604/376; 106/197.2
[58] Field of Search ................ 428/402; 604/368, 376; 536/98; 106/197.2

[56] References Cited

U.S. PATENT DOCUMENTS

| | | | |
|---|---|---|---|
| 3,371,666 | 3/1968 | Lewing | 604/376 |
| 3,375,245 | 3/1968 | Dearborn | 536/98 |
| 3,619,451 | 11/1971 | Gill | 264/109 |
| 3,621,847 | 11/1971 | Roberson | 604/376 |
| 3,654,929 | 4/1972 | Nilsson et al. | 604/376 |
| 4,091,205 | 5/1978 | Onda et al. | 536/85 |
| 4,405,324 | 9/1983 | Cruz | 604/376 |
| 4,525,585 | 6/1985 | Taguchi et al. | 536/98 |

FOREIGN PATENT DOCUMENTS 56-057719  5/1981  Japan.

Primary Examiner—George F. Lesmes
Assistant Examiner—S. A. Gibson
Attorney, Agent, or Firm—Joanne L. Horn

[57] ABSTRACT

Disclosed are novel sodium salts of carboxymethylcellulose (CMC) which are substantially nonfibrous, have a degree of substitution (D.S.) of 0.2 to 0.9 and an absorbency of at least 25 g. liquid/g. the novel CMC material, and are prepared from a cellulose furnish having a degree of polymerization (D.P.) of greater than 1,000; and to processes for preparing same. Owing to their high absorbency properties, they are particularly useful in the manufacture of disposable nonwoven products, such as adult incontinence pads, feminine hygiene products, disposable diapers and surgical dressings.

11 Claims, 2 Drawing Figures

NOVEL SALTS OF CARBOXYMETHYLCELLULOSE

This invention relates to novel substantially nonfibrous superabsorbent sodium salt of carboxymethylcellulose (referred to in the art and herein as CMC) useful in disposable nonwoven products, such as adult incontinence pads, feminine hygiene products, disposable diapers and surgical dressings, and to processes for preparing same.

Superabsorbents, as used herein, means materials capable of absorbing, and retaining under pressure, a relatively large amount of liquid, i.e., an amount greater than that absorbed by wood pulp, which is 15–20 g. liquid/g. wood pulp, and which do not plug the filter of the filtration cell apparatus (described below) used to measure the absorbency. Typically the pressure results when an individual wearing a wet incontinence pad or diaper sits down. Generally, this amount of pressure ranges from about 0.1 psi to about 1.0 psi. The liquid, referred to above and as used in this specification, means 1% sodium chloride (NaCl) in aqueous solution.

As used herein, absorbency means grams liquid absorbed per gram of material tested as determined by the Hercules Filtration Test method described herein.

Superabsorbents are used in adult incontinence pads, feminine hygiene products and disposable diapers. The effectiveness of the superabsorbents depends, to a large extent, on their ability to receive, absorb and retain liquids. Powdered superabsorbents prepared from poly(sodium acrylates) have recently been introduced in feminine hygiene products and disposable diapers. These polyacrylates have an absorbency of about 50 g. liquid/g. polymer.

In addition to the poly(sodium acrylates), prior art superabsorbents have been made from starch, starch-acrylates, and crosslinked CMC. Despite the absorptive characteristics of these materials, efforts continue to increase the absorptive characteristics of these prior art materials and/or to find other materials having absorptive characteristics greater than these prior art materials.

Conventional noncrosslinked CMCs prepared by treating a cellulose furnish with an etherifying agent, such as monochloroacetic acid, in the presence of a sodium hydroxide solution (See, e.g., Whistler, R. L., "Industrial Gums", 704–705 (2d Ed. 1973) are not superabsorbents. The CMC is purified by (1) filtering the reaction mixture to provide what is commonly referred to as an unpurified wet cake, (2) treating the wet cake with no more than 2 pounds (lbs.) water/1 lb. of cellulose, preferably less than 2 lbs. water/1 lb. cellulose, to help remove the reaction by-products, and (3) washing the resultant slurry with an aqueous solution of a nonsolvent for the CMC containing about 10% to about 50% water by weight, the ratio of nonsolvent to water being 2:1 to 5:1. The purification steps may be repeated several times depending on how pure a CMC product is desired. This mixture is then filtered and dried. These conventional CMCs appear to the naked eye to be in particulate or powder form, and have been described as being in particulate or powder form. However, when examined under a microscope at 20 times magnification, it is clear that they are actually fibrous.

Accordingly, the present invention relates to new CMCs which are substantially nonfibrous, have a degree of substitution (D.S.) of 0.2 to 0.9, have an absorbency of at least 25 g. liquid/g. the new CMC material, and are prepared from a cellulose furnish having a degree of polymerization (D.P.) of greater than 1,000. Preferably, the CMCs of this invention have a D.S. from about 0.5 to about 0.7, an absorbency of at least 50 g. liquid/g. the new CMC material, and are prepared from a cellulose furnish having a D.P. of about 1,300 to about 3,000. Most preferably, the CMCs of this invention are prepared from a cellulose furnish having a D.P. of about 1,800 to about 2,600.

There is a definite relationship between (1) absorbency and (2) (a) the particle morphology, (b) the D.S. of the CMC and (c) the D.P. of the cellulose furnish used to prepare the CMC. All must be within certain parameters to provide the new and unique CMCs of this invention having superabsorbent properties.

A substantial nonfibrous particle morphology is critical to obtaining the novel CMC of this invention having superabsorbent properties. At a minimum, 95% by weight of the CMC must be in a nonfibrous state, preferably about 99%, and most preferably >99%.

In addition, the cellulose furnish must have a D.P. of greater than 1,000 in order to be useful in the preparation of the CMC of this invention. If the D.P. of the cellulose furnish used is 1,000 or less, the resultant CMC does not have superabsorbent properties. D.P. is the number of glucose units coupled together in a particular cellulose molecule.

D.P. is measured by the ACS method set forth in "A Standard Method for Determining the Viscosity of Cellulose in Cuprammonium Hydroxide", Industrial and Engineering Chemistry, Analytical Edition, Vol. 1, 49 (Jan. 15, 1929) modified by reporting the viscosity as time in seconds required for the standard glass sphere to fall through 20, instead of 15, centimeters. The solvent system is an aqueous cuprammonium solution containing 29.5 to 30.5 g. of copper, 163 to 167 g. of ammonia, and 10 g. of sucrose per liter of solution. The concentration of cellulose used is 2.5 g. per 100 ml. of solvent.

During the preparation of the CMC, there is some degradation of the cellulose furnish as a result of alkali present. However, with conventional oxygen exclusion techniques, the degradation is minimal. Hence, the D.P. of the CMC would be marginally lower than the D.P. of the cellulose furnish used to prepare same.

The carboxymethyl D.S. is likewise necessary to obtaining the CMCs of this invention. It has not been possible to prepare a product having superabsorbent properties from a very low D.S. CMC. If the D.S. is less than 0.2, the CMC is not hydrophilic enough. If the D.S. is above 0.9, the CMC is too soluble in the liquid. Further, it has been observed that as the D.S. increases from 0.2 to 0.9, the absorbency increases, but the gel strength of the gel formed therefrom weakens.

D.S. is the average number of substituent groups, in this case carboxymethyl groups, per anhydroglucose unit in the cellulose molecule.

For a given D.P., as you raise the D.S., the CMC becomes more soluble in the liquid. For a given D.S., as you increase the D.P., it becomes less soluble in the liquid.

From the D.P., the D.S. and the sodium salt, one can calculate the approximate average molecular weight of the particular CMC.

The CMCs of this invention are prepared from chemical cotton or wood pulp having a D.P. of greater than 1,000, by etherification with monochloroacetic acid in a suitable reaction diluent in the presence of a sodium hydroxide solution, to provide CMCs having a D.S. of 0.2 to 0.9. The reaction mixture may be worked up in the conventional manner, that is, by purifying and drying as set forth above to provide a CMC in dried form; or the reaction mixture may simply be purified in the conventional manner to provide a purified CMC in wet cake form. The purified CMC, in either dried form or in wet cake form, is treated with water and mixed by tumbling in a tumbler or by stirring in a vessel equipped with a paddle or propeller stirrer, a high-speed blade mixer or other device capable of applying shear. The ratio of water:CMC used is about 10:1 to about 40:1 if the CMC used is in dry form, and is about 4:1 to about 40:1 if the CMC used is in the wet cake form. Preferably the ratio of water:CMC is about 10:1 to about 20:1 if the CMC is in the dry form, and is about 4:1 to about 10:1 if the CMC is in wet cake form. The more shear applied to mix the CMC and water, the less water one needs to add to achieve the substantially nonfibrous particle morphology. A nonsolvent for the CMC containing up to about 30% water by weight is added to the highly viscous CMC solution in a mixing vessel equipped with a propeller-type blade, the mixture is stirred, filtered and dried. The resultant product is a substantially nonfibrous, coarse, particulate material. This material is then ground in a mill using a screen of desired size. The particles have a nonfibrous content of >99% and are highly crenulated. They absorb liquids and swell, but do not dissolve.

Suitable nonsolvents for use in the preparation of the superabsorbent CMCs of this invention by any embodiment are selected from the group consisting of $C_{1-4}$ alcohols and $C_{3-4}$ ketones or mixtures thereof. Typically, the nonsolvent is acetone, methanol, isopropanol or mixtures thereof.

The nonsolvent used in the preparation of the CMCs of this invention by any embodiments in proportion to the additional water added, the ratio of nonsolvent to additional water being about 1:1 to about 10:1, preferably about 1:1 to about 2.5:1, most preferably about 1:1 to about 2:1.

Suitable reaction diluents include $C_{2-4}$ alcohols, $C_{3-4}$ ketones and mixtures thereof.

Typically, a 50% aqueous solution of sodium hydroxide is added to the cellulose furnish/monochloroacetic acid/reaction diluent mixture.

In another embodiment, the CMC of this invention is prepared by charging a blender containing 2–4 parts water with 1 part of purified CMC in wet cake form (prepared in the conventional manner as set forth above), agitating at high speed for 30 seconds, scraping the sidewalls for 30 seconds, repeating the agitation and scraping operations for a total of 5 minutes, charging the resultant paste into a mixing vessel equipped with a propeller-blade stirrer, adding 4 parts of an 100% nonsolvent for the CMC while stirring, letting the mixture stand until the solids are settled, filtering the liquid, washing the dehydrated solids with an aqueous solution of a nonsolvent for the CMC containing at least 70% of the nonsolvent and drying for 1–2 hours under vacuum at 60°–70° C. The resultant nonfibrous, coarse, solid material is then ground in a mill using a screen of desired size.

In yet another embodiment, the CMC of this invention is prepared by the conventional method as set forth above except that two or more, typically 2–5, cycles of the purification steps are used to purify the CMC. After reaction, the CMC reaction material may be treated with additional water following any one of the filtration steps in the cycles of purification steps, or after completion of the cycles of purification steps. About 4 lbs. to about 40 lbs. water/1 lb. CMC is added to the filtered, unpurified CMC wet cake. Preferably about 4 lbs. to about 20 lbs. water/1 lb. CMC is added. Most preferably about 4 lbs. to about 16 lbs. water/1 lb. CMC is added. After a single addition of water, the CMC material may be treated with additional water sequentially or nonsequentially after one or more of any of the remaining filtration steps in an amount of about 2 lbs. to about 40 lbs. The total amount of additional water added in all of the cycles of the purification steps is about 4 lbs. to about 40 lbs. water/1 lb. CMC. When the treatment(s) with additional water are complete, the resulting mixture is then treated with a suitable nonsolvent containing up to about 30% water, filtered and dried. The resultant nonfibrous, coarse, solid material is then ground in a mill using a screen of desired size. Preferably, the first portion of additional water is added after filtration in the first of the cycles of purification steps and is added in an amount of 4–5 lbs. water/1 lb. CMC. If any additional water is added after the first single addition, it is preferably added sequentially. When the CMC material is treated with additional water, preferably at least 2 lbs. water/1 lb. CMC is used.

Without being bound by the following theory, it is believed that the increased absorbency is due to the D.P. of the cellulose furnish used to prepare the CMC, the D.S. of the CMC, and to the destruction of the fibrous nature by swelling the fibers with water to form a highly viscous, pourable mixture, followed by the intermingling or entanglement of the swollen material upon contact with the nonsolvent to provide a solid, coarse particle with a high surface area which absorbs fluid and swells, but does not dissolve.

The absorbency of various conventional CMCs prepared using isopropanol as a reaction diluent, and a mixture of isopropanol (30%) and methanol (70%) as the washing solvent is shown in Table 1.

TABLE 1

| Cellulose Furnish | D.P. | D.S. | Absorbency, $g/g^a$ |
|---|---|---|---|
| Wood pulp$^b$ | 400 | 0.66 | 9.0(P)$^c$ |
| Wood pulp$^b$ | 400 | 0.61 | 5.0 |
| Wood pulp$^b$ | 400 | 0.74 | 7.0(P) |
| Wood pulp$^b$ | 400 | 0.73 | 9.0(P) |
| Wood pulp | 1500 | 0.70 | 12.0(P) |
| Wood pulp | 1500 | 0.70 | 10.5(P) |
| Wood pulp | 1500 | 0.70 | 11.0(P) |
| Wood pulp | 1800 | 0.70 | 23.0(P) |
| Chemical cotton | 2200 | 0.60 | 11.0(P) |
| Chemical cotton | 2200 | 0.60 | 12.0(P) |
| Wood pulp | 1500 | 0.90 | 16.5(P) |
| Chemical cotton | 2200 | 2.00 | 15.0(P) |
| Chemical cotton | 2200 | 0.41 | 19.0(P) |
| Chemical cotton | 2200 | 0.40 | 29.0(P) |
| Wood pulp | 1350 | 0.43 | 27.0(P) |

$^a$In 1% NaCl at 0.0 psi (1 g. polymer/99 g. NaCl solution) using Hercules Filtration Test.
$^b$Hercules CMC WS-8B which is a peroxide degraded CMC.
$^c$P means the material is a viscous material, rather than highly viscous swollen mass, which plugs the filter leaving a volume of free liquid as the top layer of the cell which is considered not to be absorbed. If the material plugs the filter, it is too soluble to be a superabsorbent.

Filtration Cell

Figure 1:
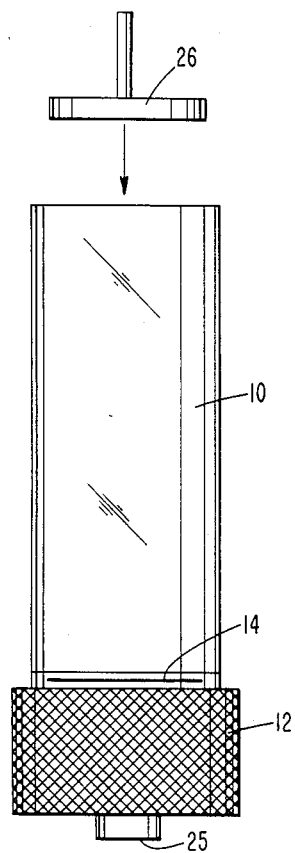
FIG. 1 shows a schematic diagram of the filtration test cell having a filter holder.
Figure 1:
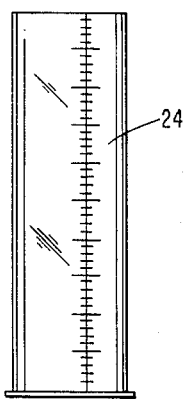

The test cell econsists of a cylindrical clear plastic chamber (10) of 2" inner diameter with the filter holder (12) attached to the bottom by a screw connection (14). The filter holder (12) contains a gasket of Teflon polymer (16) placed in a recess (17) in the bottom of the filter holder (12), which recess has an inner diameter of 2½". A filter support plate (18) having a diameter of 2⅜" and a plurality (~320) of holes, which are 1/16" in diameter, to provide for the passage of liquid is placed over the gasket (16). A single layer of gauze coverstock (20), which has been cut in a circle having a diameter of 2⅜", is placed over the filter support plate (18) to retain the absorbed material in the filter holder (12). A gasket of Teflon polymer (22) is placed over the gauze coverstock (20). The plastic chamber (10) is then mounted in the filter holder (12) by means of the screw connection (14) over the gasket (22). The gauze coverstock may be any gauze coverstock commercially available. The coverstock from the feminine hygiene napkin marketed under the trademark Sure & Natural is used in the absorbency tests set forth in this specification. The sample is poured into the plastic chamber (10) of the cell and the excess liquid collected in a collection vessel (24) as it exits the bottom opening (25) of the filter holder (12).

Absorbency Test Procedure

Figure 2:
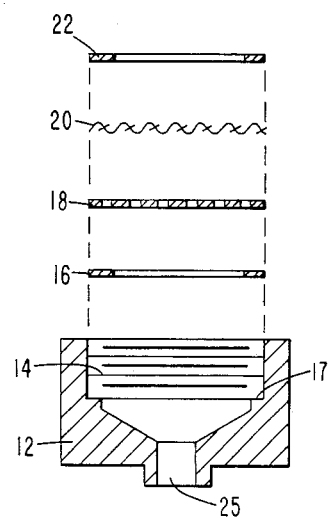
FIG. 2 is a detailed drawing partly shown in schematic form and partly shown in cross-section form illustrating the filter holder portion of the filtration test cell shown in FIG. 1.

The absorbency tests were done by the following Hercules Filtration Test using the filtration cell apparatus shown in FIGS. 1 and 2. Unless otherwise indicated, the test sample is prepared by placing 0.5 g. of the superabsorbent material in a beaker, adding 49.5 g. of a 1.0% NaCl solution, and letting the solution stand for 30 minutes. The solution is then stirred and poured into the filtration cell. The unabsorbed liquid exiting the bottom of the cell is collected over a 10 minute period and the volume of filtrate collected is recorded. The absorbency is calculated by subtracting the volume in milliliters (ml) of filtrate from 49.5 g. and multiplying the result by 2. If 1.0 g. of the superabsorbent material/99 g. NaCl solution is used, the absorbency is calculated by subtracting the volume of filtrate from 99 g. This gives the absorbency in g. of 1% NaCl solution held/g. superabsorbent material.

For purposes of this test, milliliters are deemed equivalent to grams.

If the material is viscous, it may plug the filter so as to leave a volume of free liquid as the top layer of the cell. If the material plugs the filter, it is not a superabsorbent. When plugging occurs, the absorbency is calculated by pouring off the free liquid or top layer of the cell and measuring the volume poured off. The volume of free liquid and the volume of filtrate are both subtracted from 49.5 g. The result is then multiplied by 2 to give you the absorbency.

Unless otherwise indicated, the absorbency data set forth herein is collected in the absence of any applied pressure.

Absorbency under pressure is determined by placing a metal cylinder (1⅞" diameter) (26) of known weight such that a force of 0.1 psi is applied to the top of the material in the filtration cell. The unabsorbed liquid which exits the bottom of the filtration cell is then collected for 10 minutes and the volume of filtrate recorded. The absorbency at 0.1 psi is then calculated by subtracting both the volume of filtrate collected when no pressure (0.0 psi) is applied and the volume of filtrate collected when 0.1 psi of pressure is applied from 49.5 and multiplying the result by 2. This gives the absorbency at 0.1 psi.

If the gel in the filtration cell cannot support the weight applied, the gel breaks and moves up the side of the weight between the weight and the cell wall. Since the gel is broken, no further weight is added.

If the gel supports the weight applied, additional weight in increments of 0.1 psi may be added. The volume of unabsorbed filtrate collected over 10 minutes is recorded. The absorbency is then calculated by subtracting from 49.5 the volumes of filtrate collected from (a) at no applied pressure, (b) at 0.1 psi and (c) at each of the additional increments of 0.1 psi. The result is multiplied by 2. This gives you the absorbency at a given applied pressure.

In the examples which follow, various embodiments of the superabsorbent CMCs of this invention are illustrated. Monochloroacetic acid is used as the etherifying agent in preparing the CMCs set forth in the examples.

All parts and percentages in this specification are by weight unless otherwise indicated.

EXAMPLE 1

The example illustrates the CMC of this invention and a method of preparing same.

A mixing vessel is charged with 800 ml. distilled water and 20 g. purified CMC having a D.S. of 0.6 which is prepared by the conventional method set forth herein above from a chemical cotton furnish having a D.P. of 2,300 using 50% NaOH solution as the alkali, isopropanol as the reaction diluent and a mixture of isopropanol (30%) and methanol (70%) as the washing solvent. The vessel is tumbled for ~16 hours to dissolve the CMC. The vessel is then equipped with a mechanical stirrer with a propeller-type blade, and 1,800 ml. isopropanol is then added to the highly viscous CMC solution while stirring. The resultant solid, coarse, substantially nonfibrous material is filtered through a sintered glass filter, dried in a vacuum for ~16 hours at 60° C. and ground in a Wiley mill using an 8 U.S. mesh screen. A CMC material having a nonfibrous content of >99% and superabsorbent properties is provided.

EXAMPLES 2-9

The CMCs are prepared according to the procedure of Example 1, except that the D.S. is varied as shown in Table 2.

The absorbency of the CMC materials of Examples 2-9 and the absorbency of the CMC of Example 1 are taken by the Hercules Filtration Test set forth above using the filtration cell shown in FIGS. 1 and 2. The results are set forth in Table 2 below.

TABLE 2

| Example No. | D.S. | Absorbency, g/g[a] |
|---|---|---|
| 2 | 0.1 | 15 |
| 3 | 0.2 | 25 |
| 4 | 0.3 | 46 |
| 5 | 0.4 | 51 |
| 6 | 0.5 | 58 |
| 1 | 0.6 | 72 |
| 7 | 0.7 | 96 |
| 8 | 0.8 | 93 |
| 9 | 0.9 | 96 |

[a]In 1% NaCl at 0.0 psi (0.5 g. polymer/49.5 g. NaCl solution) using the Hercules Filtration Test.

EXAMPLES 10–22

The CMCs are prepared according to the procedure of Example 1, except that (a) one portion of each CMC is ground in a Wiley mill using a U.S. 8 mesh screen, one portion using a U.S. 20 mesh screen and one portion using a U.S. 40 mesh screen, (b) the cellulose furnish having the D.P. shown in Table 3 for Examples 10–12, 14 and 16–22 is used to prepare the purified CMC instead of the chemical cotton of Example 1, and (c) the D.S. of the CMC is as shown in Table 3. The absorbency of the resultant CMCs using the Hercules Filtration Test procedure is set forth in Table 3 below.

The absorbency of several commercially available materials useful in disposable nonwoven products is determined using the Hercules Filtration Test procedure and the results are also set forth in Table 3.

TABLE 3

| | | | U.S. Mesh Screen | Nonfibrous Content, % | Absorbency (g/g)$^a$ at a Given Applied Pressure (psi) | | | |
|---|---|---|---|---|---|---|---|---|
| | D.P. | D.S. | | | 0.0 | 0.1 | 0.5 | 1.0 |
| Example No. / Cellulose Furnish | | | | | | | | |
| 10 Wood pulp | 1350 | 0.4 | 8 | >99 | 49.0 | 41.0 | 40.8(B)$^b$ | |
| | | | 20 | | 51.0 | 44.6 | 43.8(B) | |
| | | | 40 | | 52.0 | 46.2 | 45.0(B) | |
| 11 Wood pulp | 1350 | 0.4 | 8 | >99 | 47.5 | 39.9 | 38.7(B) | |
| | | | 20 | | 52.5 | 46.1 | 45.5(B) | |
| | | | 40 | | 55.5 | 50.3 | 49.3(B) | |
| 12 Chemical cotton | 1400 | 0.4 | 8 | >99 | 56.0 | 48.3 | 46.8(B) | |
| | | | 20 | | 59.5 | 50.1 | 47.9(B) | |
| | | | 40 | | 60.0 | 50.6 | 49.0(B) | |
| 13 Chemical cotton | 2250 | 0.4 | 8 | >99 | 60.0 | 48.6 | 44.2(B) | |
| | | | 20 | | 63.4 | 51.2 | 46.8(B) | |
| | | | 40 | | 64.0 | 52.0 | 49.2(B) | |
| 14 Wood pulp | 1350 | 0.3 | 8 | >99 | 40.0 | 31.8 | 28.2 | 27.6(B) |
| | | | 20 | | 40.0 | 31.8 | 29.2 | 29.0(B) |
| | | | 40 | | 41.0 | 32.8 | 31.4(B) | |
| 15 Chemical cotton | 2250 | 0.3 | 8 | >99 | 46.0 | 30.6 | 31.0 | 30.4 |
| | | | 20 | | 47.0 | 37.6 | 32.8 | 32.2 |
| | | | 40 | | 49.0 | 39.4 | 38.4 | 34.6(B) |
| 16 Chemical cotton | 1400 | 0.3 | 8 | >99 | 36.0 | 28.0 | 22.8 | 20.4 |
| | | | 20 | | 36.0 | 29.4 | 24.0 | 21.2 |
| | | | 40 | | 35.0 | 27.6 | 22.8 | 20.6 |
| 17 Chemical cotton | 2200 | 0.6 | 8 | >99 | 64.0 | 58.4 | 56.8(B) | |
| | | | 20 | | 76.0 | 69.8(B) | | |
| | | | 40 | | 80.0 | 75.0(B) | | |
| 18 Chemical cotton | 2200 | 0.6 | 8 | >99 | 72.6 | 70.8(B) | | |
| | | | 20 | | 82.0 | 78.8(B) | | |
| | | | 40 | | 80.0 | 76.4(B) | | |
| 19 40% Wood pulp | 920 | 0.4 | 8 | — | 10.0(P)$^c$ | | | |
| 60% Chemical cotton | 2250 | | 20 | | 10.0(P) | | | |
| | | | 40 | | 90.0(P) | | | |
| 20 Wood pulp | 1500 | 0.7 | 8 | — | 15.0 | 15.0 | | |
| | | | 20 | | 13.0 | 13.0 | | |
| | | | 40 | | 14.0 | 15.0 | | |
| 21 Wood pulp | 1500 | 0.7 | 8 | — | 28.0(P) | | | |
| | | | 20 | | 26.0(P) | | | |
| | | | 40 | | 30.0(P) | | | |
| 22 Wood pulp | 1500 | 0.7 | 8 | — | 25.0(P) | | | |
| Comparative Example No. / Polymer | | | | | | | | |
| I Acrylic-based material$^d$ | — | — | — | 100 | 65.0 | 51.6 | 44.0 | 43.0(B) |
| II Acrylic-based material$^e$ | — | — | — | 100 | 50.0 | 38.2 | 32.0 | 31.8 |
| III Cellulose$^f$ | — | 0.7 | — | 0 | 43.0 | 37.4 | 35.8(B) | |
| IV Cellulose$^g$ | — | 0.7 | — | 0 | 29.0 | 22.2 | 19.4 | 18.8 |
| V Acrylic-based material$^h$ | — | — | — | 100 | 65.0 | 62.6(B) | | |
| VI Cellulose$^i$ | — | ~0.7 | — | 0 | 30.0 | 24.6 | 20.8(B) | |
| VII Cellulose$^j$ | — | ~0.7 | — | 0 | 37.0 | 30.2 | 26.0(B) | |
| VIII Cellulose$^k$ | — | — | — | 0 | 15.0(P) | | | |

TABLE 3-continued

|    |            | D.P. | D.S. | U.S. Mesh Screen | Nonfibrous Content, % | Absorbency (g/g)[a] at a Given Applied Pressure (psi) | | | |
|----|------------|------|------|------------------|-----------------------|------|------|------|------|
|    |            |      |      |                  |                       | 0.0  | 0.1  | 0.5  | 1.0  |
| IX | Cellulose[l] | —  | 0.7  | —                | 0                     | 16.7 | —    | —    | 15.3 |

[a] In 1% NaCl at 0.0 psi (0.5 g. polymer/49.5 g. NaCl solution) using Hercules Filtration Test.
[b] B means the gel broke due to application of the weight. When the gel breaks, the material climbs up the side of the weight between the weight and the wall of the filter cell.
[c] P means the material is a viscous material, rather than a highly viscous swollen mass, which plugs the filter leaving a volume of free liquid as the top layer of the cell which is considered not to be absorbed.
[d] Polyacrylate marketed under the trademark Aqua-Keep by Seitetsu Kagaku Co., Ltd.
[e] Aqua-Keep material removed from Serenity contoured absorbent shield of Johnson & Johnson.
[f] Internally crosslinked CMC prepared from a chemical cotton furnish which is marketed under the trademark Aqualon grade 3C by Hercules Incorporated.
[g] Internally crosslinked CMC prepared from a chemical cotton furnish which is marketed under the trademark Aqualon grade 2C by Hercules Incorporated.
[h] Marketed under the trademark Aqualic CA by Nippon Shokubai Kagaku Kogyo Co., Ltd.
[i] Crosslinked conventional CMC marketed under the trademark Akucell grade SW3019 X-45, by Akzo NV.
[j] Crosslinked conventional CMC marketed under the trademark Akucell grade X-117, by Akzo NV.
[k] A CMC marketed under the trademark Cekosorb, grade A-10-P by Billerud AB.
[l] Internally crosslinked CMC prepared from a chemical cotton furnish which is marketed under the trademark Aqualon, grade C by Hercules Incorporated.

The gel strength is determined by measuring the elastic modulus, $G'$, at a frequency of 0.1 rad/sec using a Rheometrics mechanical spectrometer. The elastic modulus, $G'$, is measured on the material which remains in the filtration cell after removal of all the unabsorbed liquid. A gel strength of at least $3 \times 10^2$ dynes/cm$^2$ is desirable for a material useful in disposable nonwoven products. The gel strength of various CMCs of this invention and of certain commercially available materials useful in disposable nonwoven products are set forth below in Table 4.

The product, which is ground in a Wiley mill using a U.S. 8 mesh screen, is fractionated using a series of U.S. mesh screens. The effect of particle size on absorbency, gel time, and gel strength are measured and the results are set forth in Table 5.

TABLE 5

| U.S. Mesh Screen[a] | Absorbency (g/g)[b] Applied Pressure (psi) | | | Gel[c] Time (sec) | $G'$ ($\times 10^{-2}$ dynes/cm$^2$) at 0.1 rad/sec | | |
|---------------------|------|------|----------|------|------|------|------|
|                     | 0.0  | 0.1  | 0.5      |      | 0.1  | 1.0  | 10.0 sec |
| On 20               | 68.0 | 61.4 | 60.8(B)[d] | 265 | 27   | 34   | 41   |
| 40                  | 74.4 | 67.4 | 66.4(B)  | 83   | 16.5 | 20   | 25   |
| 60                  | 80.0 | 74.0(B) |       | 198  | 9    | 10.5 | 12   |
| 80                  | 82.0 | 78.0(B) |       | 367  | 8.2  | 9.3  | 10.2 |
| 100                 | 85.0 | 81.4(B) |       | >600 | 4.1  | 4.9  | 5.8  |
| 200                 | 83.0 | 78.6(B) |       | >600 | 3.5  | 4.1  | 5.0  |
| Thru 200            | 87.0 | 84.2(B) |       | >600 | 6.2  | 7.2  | 8.6  |

[a] 20 mesh = ~850μ; 40 mesh = ~425μ; 60 mesh = ~250μ; 80 mesh = ~188μ; 100 mesh = ~150μ; and 200 mesh = ~75μ. Each fraction is collected on or through the particle mesh screen which corresponds to the aforementioned particle sizes.
[b] In 1% NaCl at 0.0 psi (0.5 g. polymer/49.5 g. NaCl solution) using Hercules Filtration Test.
[c] The gel test measures the absorbency rate. The gel time is determined by placing 1 g. of the superabsorbent CMC in a vessel, adding 25 ml of 1% NaCl solution by means of a separatory funnel, and recording the time, in seconds, it takes for theCMC to totally absorb, or gel, the liquid.
[d] B means the gel broke due to application of the weight. When the gel breaks, the material climbs up the side of the weight between the weight and the wall of the filter cell.

The absorbency of the CMCs of this invention, which have been ground using a U.S. 8 mesh screen, is maximized when the CMCs have a particle size distribution such that at least 70% of the particles are retained on a U.S. 80 mesh screen and no more than 30% are passed

TABLE 4

|             | U.S. Mesh Screen | $G'$ ($\times 10^{-2}$) dynes/cm$^2$ | | | $\Delta G'$ |
|-------------|------|----------|----------|----------|----------|
|             |      | 0.1 rad/sec | 1.0 rad/sec | 10.0 rad/sec | 10.–0.1 rad/sec |
| Example No. |      |          |          |          |          |
| 10          | 8    | 52       | 63       | 70       | 18       |
| 12          | 8    | 70       | 80       | 87       | 17       |
| 13          | 8    | 90       | 100      | 111      | 21       |
| 13          | 20   | 83       | 90       | 100      | 17       |
| 13[a]       | 40   | 72       | 80       | 91       | 19       |
| 17          | 8    | 42       | 48       | 57       | 13       |
| 14          | 8    | 88       | 100      | 111      | 23       |
| 15          | 8    | 90       | 100      | 112      | 22       |
| 16          | 8    | 30       | 35       | 41       | 11       |
| 17[a]       | 40   | 52       | 67       | 67       | 15       |
| 11          | 8[b] | 58       | 67       | 75       | 17       |
| Comparative Example No. | | | | | |
| I           |      | 52       | 65       | 73       | 21       |

[a] Separate batch of the same material.
[b] Sample sieved to remove material that passes through a U.S. 100 mesh screen.

through a U.S. 100 mesh screen, preferably no more than 10% are passed through a U.S. 100 mesh screen.

The gel time indicates that the rate of absorbency is best when the particle size of the CMCs, which have been ground using a U.S. 8 mesh screen, is 100% through 20 and on 40 mesh screen. The gel strength results show that gel strength is best when the particle size of the CMCs, which have been ground using a U.S. 8 mesh screen, is 100% on 20 U.S. mesh screen.

Thus, depending on the particular product in which the substantially nonfibrous, superabsorbent CMC of this invention is used, the CMC can be adjusted to give the desired balance of properties.

EXAMPLES 23-26

These examples illustrate another embodiment of this invention.

The CMCs are prepared according to the conventional method of Example 1, except that the drying step is omitted to provide a purified wet cake having 50% CMC, 30% of the isopropanol/methanol mixture, and 20% water. The formulation of Example 1 is used except that the amount of water used to treat the purified CMC wet cake is varied as set forth in Table 6.

TABLE 6

| Example No. | ml water/10 g CMC Wet Cake | Absorbency (g/g)$^a$ at a Given Applied Pressure (psi) | | |
|---|---|---|---|---|
| | | 0.0 | 0.1 | 0.5 |
| 23 | 50 | 8.0(P)$^b$ | | |
| 24 | 100 | 47.0 | 43.0(B)$^c$ | |
| 25 | 200 | 55.5 | 49.7 | 48.3(B) |
| 26 | 400 | 71.5 | 63.5 | 60.7(B) |

$^a$In 1% NaCl at 0.0 psi (0.5 g. polymer/49.5 g. NaCl solution) using the Hercules Filtration Test.
$^b$P means the material is a viscous material, rather than highly viscous swollen mass, which plugs the filter leaving a volume of free liquid as the top layer of the cell which is considered not to be absorbed.
$^c$B means the gel broke due to application of the weight. When the gel breaks, the material climbs up the side of the weight between the weight and the wall of the filter cell.

EXAMPLE 27

This example illustrates another embodiment of this invention.

A purified CMC wet cake is prepared according to the procedure of Example 1 except that acetone was used as the reaction diluent and washing solvent, and except that the drying step is omitted. A Waring blender containing 50 ml. water is charged with 10 g. purified CMC, prepared from a chemical cotton furnish having a D.P. of 2,300, in wet cake form containing, by weight, 50% CMC having a D.S. of 0.6 and a D.P. of 2,300, 30% acetone and 20% water. The ingredients are agitated for 30 seconds and the sides of the blender are scraped for 30 seconds. The agitation and scraping are repeated in this manner for five minutes. The resultant material is a paste. The paste is placed in a mixing vessel equipped with a propeller blade stirrer. Stirring is commenced and 200 ml. of 100% acetone is added. Once the addition is complete, the stirring is continued for 5-15 minutes. The mixture is then left standing until the solids settle (~15 minutes).

The liquid is filtered off and the solids are then dried in a vacuum oven for 16 hrs. at 60° C. The resultant coarse, substantially nonfibrous material is then ground through a U.S. 8 mesh screen in a Wiley mill. The product has a nonfibrous content of >99%.

EXAMPLES 28-30

The CMCs are prepared according to the procedure of Example 27 using the formulation of Example 27 except that the amount of water used is varied as set forth in Table 7. The absorbency of these superabsorbent CMCs is shown in Table 7.

TABLE 7

| Example No. | ml water/10 g CMC Wet Cake | Absorbency (g/g)$^a$ at a Given Applied Pressure (psi) | | |
|---|---|---|---|---|
| | | 0.0 | 0.1 | 0.5 |
| 27 | 50 | 49.0 | 39.8 | 38.2(B)$^b$ |
| 28 | 100 | 51.0 | 44.4 | 44.2(B) |
| 29 | 200 | 68.0 | 63.4 | 62.0(B) |
| 30 | 400 | 73.0 | 64.8 | 63.2(B) |

$^a$In 1% NaCl at 0.0 psi (0.5 g. polymer/49.5 g. NaCl solution) using the Hercules Filtration Test.
$^b$B means the gel broke due to application of the weight. When the gel breaks, the material climbs up the side of the weight between the weight and the wall of the filter cell.

EXAMPLES 31-32

These examples illustrate another embodiment of this invention.

The CMCs having the D.S. set forth in Table 8 are prepared by the conventional method set forth herein from the cellulose furnish having the D.P. set forth in Table 8 except that three cycles of the purification steps are used and acetone is used both as the reaction diluent and washing solvent and except that the drying step is omitted.

Separate 50 g. portions of the purified wet cake containing 60% CMC, 40% acetone and 10% water is treated with the amount of water shown in Table 8 in a mixing vessel and mixed. The slurry is then charged to a reslurry vessel equipped with a stirrer. Acetone (100%) is added while stirring. The mixture is filtered and the resultant product. is dried in a conventional manner. The substantially nonfibrous coarse material is ground in a Wiley mill with a U.S. 8 mesh screen. The CMC material has a nonfibrous content of about 99% and superabsorbent properties.

EXAMPLE 33

This example illustrates another embodiment of this invention.

The CMC having the D.S. set forth in Table 8 is prepared by the conventional method set forth herein from the cellulose furnish having the D.P. set forth in Table 8 using acetone as the reaction diluent except that prior to the purification steps, the reaction mixture is filtered to provide an unpurified wet cake. Separate 50 g. portions of the unpurified wet cake are treated with the amount of water set forth in Table 8 in a mixing vessel and mixed. The slurry is then charged to a reslurry vessel equipped with a stirrer. Acetone (100%) is added while stirring. The mixture is then purified and dried in the conventional manner. The substantially nonfibrous coarse material is ground in a Wiley mill with a U.S. 8 mesh screen. The CMC material has a nonfibrous content of about 99% and superabsorbent properties.

EXAMPLE 34

This example illustrates another embodiment of this invention.

The CMCs having the D.S. set forth in Table 8 is prepared by the conventional method set forth herein from the cellulose furnish having the D.P. set forth in Table 8 using acetone as the reaction diluent and washing solvent except that the drying step is omitted. Separate 50 g. portions of the purified wet cake are treated with the amount of water set forth in Table 8 in a mixing vessel and mixed. The slurry is then charged to a reslurry vessel equipped with a stirrer. Acetone (100%) is added while stirring. The mixture is then purified in the conventional manner two more times using an aqueous solution of acetone containing 30% water and then dried in the conventional manner. The substantially nonfibrous coarse material is ground in a Wiley mill with an 8 mesh screen. The CMC material has a nonfibrous content of about 99% and superabsorbent properties.

TABLE 8

| Example No. | D.P. | D.S. | Cellulose Furnish | lbs. water/ 1 lb. CMC | Absorbency (g/g)$^a$ at a Given Applied Pressure (psi) 0.0 |
|---|---|---|---|---|---|
| 31 | 1850 | 0.62 | Wood pulp | 4 | 54.0 |
|  | 1850 | 0.62 | Wood pulp | 8 | 57.5 |
|  | 1850 | 0.62 | Wood pulp | 12 | 63.5 |
|  | 1850 | 0.62 | Wood pulp | 16 | 75.0 |
| 32 | 1500 | 0.67 | Wood pulp | 4 | 46.5 |
|  | 1500 | 0.67 | Wood pulp | 8 | 45.5 |
|  | 1500 | 0.67 | Wood pulp | 12 | 54.0 |
|  | 1500 | 0.67 | Wood pulp | 16 | 58.5 |
| 33 | 1500 | 0.67 | Wood pulp | 4 | 41.0 |
|  | 1500 | 0.67 | Wood pulp | 8 | 49.0 |
|  | 1500 | 0.67 | Wood pulp | 12 | 64.0 |
|  | 1500 | 0.67 | Wood pulp | 16 | 74.5 |
| 34 | 1500 | 0.67 | Wood pulp | 4 | 49.5 |
|  | 1500 | 0.67 | Wood pulp | 8 | 49.0 |
|  | 1500 | 0.67 | Wood pulp | 12 | 57.0 |
|  | 1500 | 0.67 | Wood pulp | 16 | 73.5 |

$^a$In 1% NaCl at 0.0 psi (0.5 g. polymer/49.5 g. NaCl solution) using Hercules Filtration Test.

Thus, this invention provides a unique substantially nonfibrous CMC having improved superabsorbent properties.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A CMC material comprising a minimum of 95% of nonfibrous particulate CMC material having an absorbency of at least 25 g. liquid/g. nonfibrous particulate CMC material, prepared by treating a CMC having a D.S. of 0.2 to 0.9 produced from a cellulose furnish having a D.P. of greater than 1,000 with water wherein the ratio of water:CMC is about 4:1 to about 40:1 when the CMC is in wet cake form and wherein the ratio of water: CMC is about 10:1 to about 40:1 when the CMC is in dry form.

2. The CMC material of claim 1 wherein the ratio of water:CMC is about 4:1 to about 10:1 when the CMC is in wet cake form and wherein the ratio of water:CMC is about 10:1 to about 20:1 when the CMC is in dry form.

3. The material of claim 1 wherein the CMC has a D.S. from about 0.5 to about 0.7 and an absorbency of at least 50 g. liquid/g. material, and which is prepared from a cellulose furnish having a D.P. of about 1,300 to about 3,000.

4. The material of claim 1 wherein the CMC ground using a U.S. 8 mesh screen has a particle size distribution such that at least 70% of the particles are retained on an 80 mesh screen and no more than 30% are passed through an 100 mesh screen.

5. The material of claim 4 wherein the CMC ground using a U.S. 8 mesh screen has a particle size distribution such that not more than 10% are passed through an 100 mesh screen.

6. The material of claim 3 wherein the CMC ground using a U.S. 8 mesh screen has a particle size distribution such that at least 70% of the particles are retained on an 80 mesh screen and no more than 30% are passed through an 100 mesh screen.

7. The material of claim 6 wherein the CMC ground using a U.S. 8 mesh screen has a particle size distribution such that not more than 10% are passed through an 100 mesh screen.

8. The material of claim 1 wherein the CMC ground using a U.S. 8 mesh screen has a particle size such that 100% is through U.S. 20 and on U.S. 40 mesh screen.

9. The material of claim 3 wherein the CMC ground using a U.S. 8 mesh screen has a particle size that 100% is through U.S. 20 and on U.S. 40 mesh screen.

10. The material of claim 1 wherein the CMC ground using a U.S. 8 mesh screen has a particle size such that 100% is on U.S. 20 mesh screen.

11. The material of claim 3 wherein the CMC ground using a U.S. 8 mesh screen has a particle size such that 100% is on U.S. 20 mesh screen.

* * * * *